(12) United States Patent
Zielenski

(10) Patent No.: US 7,300,769 B2
(45) Date of Patent: Nov. 27, 2007

(54) STABILIZED COENZYME SOLUTIONS FOR DETERMINING DEHYDROGENASE ACTIVITY

(75) Inventor: Ralf Zielenski, Benediktbeuern (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 11/056,700

(22) Filed: Feb. 11, 2005

(65) Prior Publication Data

US 2005/0136505 A1 Jun. 23, 2005

Related U.S. Application Data

(62) Division of application No. 09/760,205, filed on Jan. 12, 2001, now abandoned.

(30) Foreign Application Priority Data

Jan. 15, 2000 (DE) .................. 100 01 529

(51) Int. Cl.
*C12Q 1/32* (2006.01)
(52) U.S. Cl. ........................................ 435/26
(58) Field of Classification Search .................. None
See application file for complete search history.

(56) References Cited

U.S. PATENT DOCUMENTS

| | | | | |
|---|---|---|---|---|
| 3,732,147 A | * | 5/1973 | Fosker et al. | 435/26 |
| 5,206,147 A | * | 4/1993 | Hoenes | 435/25 |
| 5,397,699 A | * | 3/1995 | Davis et al. | 435/7.94 |
| 5,424,204 A | * | 6/1995 | Aoyama et al. | 435/188 |
| 5,871,949 A | * | 2/1999 | Ebinuma et al. | 435/26 |

FOREIGN PATENT DOCUMENTS

| | | |
|---|---|---|
| EP | 0804610 B1 | 11/1997 |
| JP | 62278997 A * | 12/1987 |
| RU | 1837236 A1 * | 8/1993 |

OTHER PUBLICATIONS

Brooks et al. An Automated Fluorometric Method for Determination of Lactic Dehydrogenase in Serum; Clinical Chemistry, vol. 11 (1965) pp. 748-762.*
Ionization Constants of Organic Acids (http://www.cem.msu.edu/~reusch/VirtualText/acidity2.htm), downloaded from the internet on Jan. 19, 2007.*
Renze Bais, et al., "Approved Recommendation of IFCC Methods for the Measurement of Catalytic Concentration of Enzymes," IFCC Jan. 1994: Enzymes, VII, IFCC Method for Lactate Dehydrogenase, Eur. Clin. Chem. Clin. Biochem. vol. 32, 1994, pp. 639-655, International Federation of Clinical Chemistry (IFCC)1,2).
K. Lorentz, et al., "Recommendation of the Determination of the Catalytic Concentration of Lactate Dehydrogenase at c7C," Recommendation: Lactate dehydrogenase assay at 37C, Eur. J. Clin. Chem. Clin. Biochem. vol. 31, 1993, pp. 897-899.
JP 84/82398, Derwent-Abstract.

* cited by examiner

*Primary Examiner*—Jon Weber
*Assistant Examiner*—Paul Martin
(74) *Attorney, Agent, or Firm*—Dinsmore & Shohl LLP

(57) ABSTRACT

Stabilized aqueous solution of a coenzyme for hydrogen-transferring enzymes characterized in that the solution contains NAD, NADP or a derivative thereof in an oxidized or reduced form and one or several organic compounds or salts thereof having a pKa value between 1.5 and 6.0 and/or a nitrogen compound of the general formula

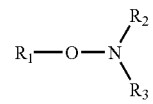

in which the residues $R_1$, $R_2$ and $R_3$ are the same or different and denote hydrogen, or a saturated or unsaturated alkyl or aryl group as well as the use of the solution to determine dehydrogenases in particular lactate dehydrogenase or substrates thereof.

14 Claims, No Drawings

STABILIZED COENZYME SOLUTIONS FOR DETERMINING DEHYDROGENASE ACTIVITY

This application is a divisional of Ser. No. 09/760,205 filed Jan. 12, 2001, now abandoned.

FIELD OF THE INVENTION

The invention concerns stabilized aqueous solutions of a coenzyme for hydrogen-transferring enzymes and their use for determining a corresponding analyte (substrate) in a reduced form or for determining the enzyme activity of a corresponding dehydrogenase. The stabilized solution contains an organic compound or appropriate salts having a pKa value between 1.5 and 6.0 and/or a hydroxylamine derivative.

BACKGROUND

The determination of enzyme activities (or substrate concentrations), especially in blood serum or plasma, plays an important role in clinical chemical diagnostics. Test procedures are often used for this which are based on the reduction of nicotinamide adenine dinucleotide (NAD) or nicotinamide adenine dinucleotide phosphate (NADP) and photometric detection of the resulting change of the absorption behaviour in the ultraviolet wavelength range ($\lambda$=334, 340 or 365 nm). When suitable test conditions have been selected, this change is linearly proportional to the enzyme activity (or substrate concentration) to be determined.

Nowadays the methods described in *Eur. J. Clin. Chem. Clin. Biochem.* 31, 897 (1994) and *Eur. J. Clin. Chem. Clin. Biochem.* 32, 639 (1994) are generally recommended for determining the enzyme activity of for example lactate dehydrogenase (LDH, E.C.1.1.1.27). The test principle involves the oxidation of lactate to pyruvate while a coenzyme such as NAD or NADP is simultaneously reduced to NADH or NADPH. Such a conversion, in this case is for example catalysed by LDH, takes place in an alkaline medium (pH 9.4). As a result of this instability there is a relatively rapid increase in absorbance (the so-called reagent blank) in the wavelength range for the measurement and hence the reagent combination becomes unusable already after a short time (3 months) even when stored in a refrigerator (2° to 8° C.). This is a particular problem for the production of ready-to-use liquid reagents with a long shelf-life which are intended to enable the user to carry out analyses in the daily routine in a simple and reliable manner.

A method for stabilizing aqueous coenzymes using chelating agents and azides is known from JP 84/82398. However, a disadvantage of this method is that it is necessary to add azide which is nowadays classified as cancerogenic and which, moreover, has an inhibitory effect on many enzymes.

It is also known that coenzyme solutions can be stabilized by adding heavy metal salts, for example in the form of copper (II) ions, and thus prevent an increase of the reagent blank (DE 195 43 493 or EP 0 804 610). However, degradation products may form during long storage periods or at high storage temperatures (already above 10° C.) which inhibit the dehydrogenase enzyme to be determined and thus result in measured values that are too low. A reagent that can be stabilized over a long period (3 months and more) of constant quality which thus, among other things, does not require repeated calibrations is not available at present.

DESCRIPTION OF THE INVENTION

Hence the object of the present invention is to provide an improved stable liquid reagent containing a coenzyme for hydrogen-transferring enzymes which is suitable for determining dehydrogenase activity or corresponding substrates.

The object is achieved by an aqueous solution which contains a coenzyme for hydrogen-transferring enzymes such as NAD, NADP or an appropriate derivative in an oxidized or reduced form (so-called regenerating systems) and one or several organic compounds or salts derived therefrom with a pKa value between 1.5 and 6.0 and/or a nitrogen compound of the general formula

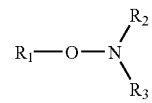

in which the residues $R_1$, $R_2$ and $R_3$ are the same or different and denote hydrogen, a saturated or unsaturated alkyl or aryl group. Suitable alkyl groups are in particular those which have one to ten carbon atoms. Furthermore the alkyl groups can be straight-chained or branched. Suitable aryl groups according to the invention are substituted or unsubstituted phenyl groups which are optionally bound via an alkenyl group which can have 1 to 8 carbon atoms. Nitrogen compounds of the said general formula, i.e., in particular hydroxylamine derivatives such as hydroxylamine, O- or N-alkylhydroxylamine having one to six carbon atoms or O-benzylhydroxylamine or salts derived therefrom such as sulfates, phosphates or ammonium salts have proven to be particularly suitable according to the invention. In addition suitable hydroxylamine derivatives are characterized by a complexing effect towards the degradation products of the coenzyme.

In addition the stability of the solutions can be further improved when the solution additionally contains a complexing agent i.e. a ligand which has two or more coordination positions. Bidentate ligands such as ethylene diamine and tetradentate or multidentate ligands such as ethylenediamine-N,N,N,N-tetraacetic acid (EDTA) or appropriate salts thereof, especially the disodium salt, crown ethers or cryptands have proven to be advantageous. This corresponds to a concentration of the complexing agent of about 0.5 to 30 mM, preferably of 1.0 to 5.0 mM.

Organic compounds or salts derived therefrom that are added according to the invention with a pKa value between ca. 1.5 and 6.0 are especially organic acids which have a complexing action and a buffering action in the pH range of 1.0 to 7.0 such as citric acid and water-soluble salts derived therefrom.

The concentrations of the organic compounds, salts or hydroxylamine derivatives that are to be added according to the invention can vary within wide limits i.e. between ca. 0.001 and 1.0 M. A concentration of ca. 5 to 200 mM has proven to be particularly suitable for citric acid or citrate. In numerous cases ca. 50 mM citric acid or citrate already resulted in the desired effect. The preferred concentration range for the hydroxylamine derivative according to the invention that is to be added in addition to or in the absence of an organic compound with a suitable pKa value is between about 2 and 300 mM. The pH value of the stabilized aqueous solution can be between 1.0 and 7.0, a pH value between ca. 2.0 and 4.0 or of ca. 3.0 having proven to be particularly advantageous.

Moreover, it has proven to be particularly advantageous when the reagent containing NAD or NADP contains a hydroxylamine derivative and optionally additionally a citrate salt and when boric acid or a borate salt is additionally present in an optional further reagent that may be necessary to determine corresponding hydrogen-transferring analytes that contains in particular buffers necessary for the determination such as N-methylglucamine (MEG), substrates and optionally other auxiliary substances. The concentrations set forth above also apply to this special embodiment. Furthermore, ca. 20 to 200 mM have proven to be particularly advantageous for citrate or citric acid and ca. 10 to 150 mM for the respective hydroxylamine derivative. A concentration range of ca. 50 to 200 mM has proven to be particularly suitable for the boric acid derivative which is preferably added to the substrate solution (so-called reagent 1) which does not contain NAD or NADP.

Substances which have a good buffer capacity between ca. pH 8.5 and 10.0 such as the so-called Good buffers (tricine, bicine, TAPS, AMPSO, CHES, CAPSO, AMP, CAPS), carbonates of alkali metal ions, MEG, TRIS and phosphate buffer are basically suitable as buffers for the reagent containing substrate. Mixtures of the said buffer substances have also proven to be suitable for the solution according to the invention. In addition it has proven to be advantageous when the buffer concentration is between ca. 10 and 1000 mM, preferably between 200 and 600 mM. Furthermore, the addition of boric acid or soluble salts and derivatives thereof to the alkaline buffer solution (reagent 1) which primarily determines the working pH value has proven to be advantageous. The concentration of suitable boric acid components is preferably between about ca. 50 and 200 mM, particularly preferably about 100 mM.

Suitable coenzymes in the sense of the present invention are in particular NAD and NADP, and also modified coenzymes such as thioNAD(P) or NHxDP (nicotinamide hypoxanthine dinucleotide phosphate). The coenzymes can be present at a concentration of approximately 1.0 to 100 mM in the reaction cuvette; a range of 5.0 to 15.0 mM is preferred.

The stabilized coenzyme solutions according to the invention are preferably used in the form of aqueous solutions. Furthermore the ready-to-use reagent is also stable over a wide time period as a granulate, powder mixture and as a lyophilisate. Thus no signs of reagent decomposition whatsoever are found at temperatures of 2° to 8° C. within 15 months. Under stress i.e. at a temperature of ca. 35° C. for 2 weeks or treatment at ca. 42° C. for five days, it was shown that the solution containing one or several additives according to the invention remained qualitatively unchanged i.e. stable.

A further subject matter of the invention is a method for determining a hydrogen-transferring analyte or a corresponding dehydrogenase in the presence of a hydrogen accepting coenzyme wherein the coenzyme is present in a stabilized aqueous solution as described above.

The determination is carried out in particular in samples of biological origin such as whole blood, serum or plasma, or other human or animal sources or in plant extracts. The sample can be prepared using physiological saline. In such a case a 0.9% NaCl solution is advantageously used as a control value.

If it is intended to determine the enzyme activity of a dehydrogenase such as a lactate dehydrogenase, a substrate solution e.g. a lactate solution in a substance (mixture) buffering at ca. pH 9.4 (37° C.) is used. In this case the substrate can be used in the usual concentrations known to a person skilled in the art, preferably in a range of 40 to 80 mM.

In order to determine a hydrogen-transferring analyte such as lactate, the respective dehydrogenase, e.g. LDH, is added first in a substance buffering between pH 8.5 and 10.0. Usually a dehydrogenase quantity of approximately 70 to 500 U/l, preferably of 110 to 220 U/l is sufficient. The determination is usually carried out at ca. 37° C.

In addition to lactate which was described as an example, it is also possible to similarly determine glutamate or ammonia, alcohol, glyceraldehyde-3-phosphate, glucose or other parameters that can be converted by a suitable coenzyme-dependent dehydrogenase. This applies in a corresponding manner to the determination of the enzyme activity of such dehydrogenases.

A further subject matter of the invention is a so-called test kit for carrying out the enzyme or analyte determination. The kit is essentially compose □ of two partial reagents. If it is used to determine the activity of a dehydrogenase, the first reagent contains a hydrogen-transferring analyte (substrate) in a suitable system buffering between pH 8.5 and 10.0. The second reagent has a coenzyme for hydrogen-transferring enzymes such as NAD or NADP and an organic compound having a pKa value between 1.5 and 6.0 and/or a hydroxylamine derivative according to the invention. The second reagent can additionally contain other auxiliary substances such as heavy metal salts or a complexing agent. This applies correspondingly to the determination of an analyte or substrate such as lactate.

The invention is further elucidated by the following examples:

| Abbreviations | |
|---|---|
| AMP | 2-amino-2-methyl-1-propanol |
| AMPSO | 3-[(1,1-dimethyl-2-hydroxyethyl)amino-2-hydroxypropanesulfonic acid |
| bicine | N,N-bis[2-hydroxyethyl]glycine |
| CAPS | 3-[cyclohexylamino]-1-propanesulfonic acid |
| CAPSO | 3-[cyclohexylamino]-2-hydroxy-1-propanesulfonic acid |
| CHES | 2-[N-cyclohexylamino]ethanesulfonic acid |
| MEG | N-methylglucamine |
| TAPS | N-tris[hydroxymethyl]methyl-3-aminopropanesulfonic acid |
| Tricine | N-tris[hydroxymethyl]methylglycine |
| TRIS | 2-amino-2-(hydroxymethyl)-1,3-propanol |

EXAMPLE 1

Reagent 1: 390 mmol/l N-methylglucamine, pH 9.4 (37° C.); 60 mmol/l lithium L-lactate Reagent 2: 60 mmol/l NAD(P) as a lyophilisate, powder mixture, granulate or aqueous solution Incubation temperature: 37°±0.1° C.; measurement wavelength: 340±2 nm; path length: 7 mm Preincubation: 5 minutes; lag phase: 2 minutes; measurement time: 2 minutes Reagent 1: 250 µl; reagent 2: 50 µl; sample: 7 µl; NaCl solution (0.9% w/v)

The following determinations were carried out (IFCC-recognized reference for the determination of LDH containing lactate, NAD/NADP and N-methylglucamine, pH 9.4; *Eur. J. Clin. Chem. Biochem.* 32, p. 639-655, 1994):

TABLE 1

| Reagent 1 | Reagent 2 | Blank value (BV) unstressed [mA/min] | Blank value (BV) 5 days, 42° C. [mA/min] | Calibrator signal - BV unstressed [mA/min] | Calibrator signal - BV 5 days 42° C. [mA/min] |
|---|---|---|---|---|---|
| IFCC + 100 mmol/l borate | IFCC | 1.3 | 6.3 | 32.4 | 31.0 = 95.7% |
| IFCC | IFCC + 100 mmol/l citrate pH 3.0 | 2.1 | 6.2 | 35.2 | 33.4 = 95.4% |
| IFCC + 100 mmol/l borate | IFCC + 100 mmol/l citrate pH 3.0 | 1.0 | 3.0 | 30.9 | 29.4 = 95.1% |
| IFCC | IFCC + 50 mmol/l hydroxylamine | 0.9 | 3.2 | 34.4 | 33.8 = 98.3% |
| IFCC + 100 mmol/l borate | IFCC + 50 mmol/l hydroxylamine | 0.7 | 1.8 | 31.1 | 30.5 = 98.0% |
| IFCC + 100 mmol/l borate | IFCC + 50 mmol/l hydroxylamine + 100 mmol/l citrate pH 3.0 | 0.7 | 1.2 | 29.8 | 30.3 = 101.7% |
| IFCC (prior art) | IFCC | 1.5 | 11.5 | 35.7 | 33.7 = 94.5% |

Result: The inventive formulation containing appropriate additives in the partial reagent 1 and/or partial reagent 2 shows a considerably improved blank value with an almost unchanged calibrator blank value compared to the IFCC reference method especially under stress (5 days, 42° C.).

EXAMPLE 2

The initial solutions described in example 1 and the corresponding procedures were used. Citrate and/or various hydroxylamine derivatives in different concentrations and combinations were added to reagent 2 (table 2).

TABLE 2

| Reagent 1 | Reagent 2 | Blank value (BV) unstressed [mA/min] | Blank value (BV) 5 days, 42° C. [mA/min] | Calibrator signal - BV unstressed [mA/min] | Calibrator signal - BV 5 days 42° C. [mA/min] |
|---|---|---|---|---|---|
| IFCC = reference | IFCC = reference | 0.1 | 10.7 | 35.7 | 32.9 = 92.1% |
| IFCC | IFCC + 20 mmol/l citrate + 50 mmol/l hydroxylamine sulfate | 0.8 | 2.5 | 31.6 | 31.2 = 98.7% |
| IFCC | IFCC + 20 mmol/l citrate + 50 mmol/l hydroxylamine phosphate | 0.6 | 1.7 | 30.9 | 30.2 = 98.1% |
| IFCC | IFCC + 20 mmol/l citrate + 50 mmol/l O-benzyl-hydroxylamine | −0.9 | −0.6 | 34.8 | 33.3 = 95.7% |
| IFCC | IFCC + 20 mmol/l citrate + 50 mmol/l O-methyl-hydroxylamine | −0.7 | 0.0 | 35.2 | 33.6 = 95.5% |
| IFCC | IFCC + 20 mmol/l citrate + 50 mmol/l N-methyl-hydroxylamine | 4.9 | 11.1 | 34.6 | 34.6 = 100.0% |

Result: All compounds and salts added to the inventive reagent 2 resulted in an improved recovery after stress (5 days, 42° C.) compared to the IFCC reagent.

EXAMPLE 3

The recovery of the various isoenzymes was also demonstrated using the formulation according to the invention. This must correspond to the recovery of the recognized IFCC recommendation (table 3).

The determinations were carried out using the IFCC reagent described in example 1 (prior art) compared to a reagent according to the invention.

TABLE 3

| Reagent 1 | Reagent 2 | Activity isoenzyme 1 [U/l] | Activity isoenzyme 2 [U/l] | Activity isoenzyme 3 [U/l] | Activity isoenzyme 4 [U/l] | Activity isoenzyme 5 [U/l] |
|---|---|---|---|---|---|---|
| IFCC | IFCC | 536 | 528 | 735 | 325 | 382 |
| IFCC + 100 mmol/l borate | IFCC + 50 mmol/l hydroxylamine + 100 mmol/l citrate pH 3.0 | 536 | 523 | 736 | 301 | 368 |

Result: The recovery of the five LDH isoenzymes was demonstrated with the reagent according to the invention.

If the said modifications were carried out on the formulation, it is possible to provide a liquid LDH reagent which remains stable during storage (>12 months) and transport (even at temperatures >8° C.). The resulting advantages for the user are obvious and are shown in the description of the invention.

What is claimed is:

1. A method for determining the activity of lactate dehydrogenase (LDH) in a sample comprising:
   (a) providing a first reagent comprising a hydrogen-transferring substrate for the LDH;
   (b) providing a second reagent comprising a hydrogen-accepting coenzyme selected from the group consisting of NAD, NADP and derivatives thereof, and one or more compounds selected from the group consisting of citric acid or a citrate salt and nitrogen compounds of the formula

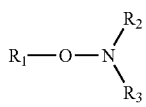

in which $R_1$, $R_2$ and $R_3$ are the same or different and denote hydrogen or a saturated or unsaturated alkyl or aryl group;
   (c) forming a reaction mixture by combining the sample with the first reagent and the second reagent, and
   (d) detecting the change in absorbance of the coenzyme as a measure of the activity of the LDH present in the sample.

2. The method of claim 1 wherein the second reagent comprises the citric acid or citrate salt in a concentration of about 5 to 200 mM.

3. The method of claim 1 wherein the pH of the first reagent is between about 8.5 and 10.0.

4. The method of claim 1 wherein the nitrogen compound is a hydroxylamine derivative or salt thereof.

5. The method of claim 4 wherein the second reagent comprises the hydroxylamine derivative or salt in a concentration of between about 2 and 300 mM.

6. The method of claim 1 wherein the first reagent mixture further comprises a boric acid or a borate salt.

7. The method of claim 6 wherein the concentration of the boric acid or borate salt is about 50 to 200 mM.

8. A kit for determining the activity of lactate dehydrogenase (LDH) in a sample comprising:
   (a) a first reagent comprising a hydrogen-transferring enzyme for the LDH and a buffer having a pH between about 8.5 and 10.0 and
   (b) a second reagent comprising a hydrogen-accepting coenzyme selected from the group consisting of NAD, NADP and derivatives thereof: one or more compounds selected from the group consisting of citric acid and a citrate salt; and one or more nitrogen compounds of the formula

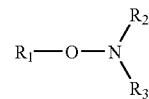

in which $R_1$, $R_2$ and $R_3$ are the same or different and denote hydrogen or a saturated or unsaturated alkyl or aryl group.

9. The kit of claim 8 wherein the concentration of the citric acid or citrate salt is about 5 to 200 mM.

10. The kit of claim 8 wherein the second reagent has a pH between about 1.0 and 7.0.

11. The kit of claim 8 wherein the nitrogen compound is a hydroxylamine derivative or salt thereof.

12. The kit of claim 11 wherein the concentration of the hydroxylamine derivative or salt is about 2 to 300 mM.

13. The kit of claim 8 wherein the first reagent further comprises a boric acid derivative.

14. The kit of claim 13 wherein the concentration of the boric acid derivative is about 50 to 200 mM.

* * * * *